US005489284A

United States Patent [19]
James et al.

[11] Patent Number: 5,489,284
[45] Date of Patent: Feb. 6, 1996

[54] CANNULATED MODULAR INTRAMEDULLARY NAIL

[75] Inventors: Anthony James, Bartlett, Tenn.; Harry Lee, South Haven, Miss.; John R. Pepper, Germantown; Thomas A. Russell, Memphis, both of Tenn.

[73] Assignee: Smith & Nephew Richards Inc., Memphis, Tenn.

[21] Appl. No.: 275,636

[22] Filed: Jul. 15, 1994

[51] Int. Cl.⁶ ........................................ A61B 17/72
[52] U.S. Cl. .............................. 606/62; 606/64
[58] Field of Search .................. 606/62, 63, 64, 606/65, 66, 67, 68; 623/23; 411/479, 469

[56] References Cited

U.S. PATENT DOCUMENTS

| | | |
|---|---|---|
| 3,846,846 | 11/1974 | Fischer . |
| 4,622,959 | 11/1986 | Marcus . |
| 4,776,330 | 10/1988 | Chapman et al. . |
| 4,805,607 | 2/1989 | Engelhardt et al. . |
| 4,827,917 | 5/1989 | Brumfield . |
| 4,858,601 | 8/1989 | Glisson . |
| 4,875,475 | 10/1989 | Comte et al. . |
| 4,940,467 | 7/1990 | Tronzo ........................... 606/66 |
| 4,995,883 | 2/1991 | Demane et al. ................. 623/23 |
| 5,047,033 | 9/1991 | Fallin ............................. 606/87 |
| 5,074,882 | 12/1991 | Grammont et al. ............. 606/63 |
| 5,098,435 | 3/1992 | Stednitz et al. ................ 606/73 |
| 5,108,452 | 4/1992 | Fallin ............................. 623/23 |
| 5,116,378 | 5/1992 | Carbone ......................... 623/23 |
| 5,122,141 | 6/1992 | Simpson et al. ................ 606/62 |
| 5,352,227 | 10/1994 | O'Hara ........................... 606/63 |

FOREIGN PATENT DOCUMENTS 1031128  6/1953  France .

Primary Examiner—Stephen C. Pellegrino
Assistant Examiner—Scott B. Markow
Attorney, Agent, or Firm—Pravel, Hewitt, Kimball & Krieger

[57]  ABSTRACT

A modular intramedullary nail includes three connectable sections that are connectable end to end. The three sections include an upper proximal nail component having an open ended bore. The second section is a central nail section that is an elongated curved nail component having an open ended longitudinal bore. The third section is a lower distal nail component having an elongated open ended longitudinal bore. The nail components are connected and the end using corresponding conical socket and conical projecting end portions of adjoining end nail components that can be fitted together and secured upon impact. Upon assembly, the connections are self orienting, providing corresponding tooled "flat" portions adjacent the respective conical socket and conical projecting end portions of the nail components. This interlocking tooled flats align and abut upon assembly so that the adjoining nail components only align in one relative rotational position. The assembled nail thus provides an elongated continuous open ended bore that receives a cannulated fastener. The fastener extends the full length of the longitudinal bore of the assembled three nail sections. An upper enlarged head portion of the cannulated fastener grips the proximal nail component. The distal end portion of the cannulated fastener has external threads which engage corresponding internal threads within the bore of the distal nail component.

19 Claims, 6 Drawing Sheets

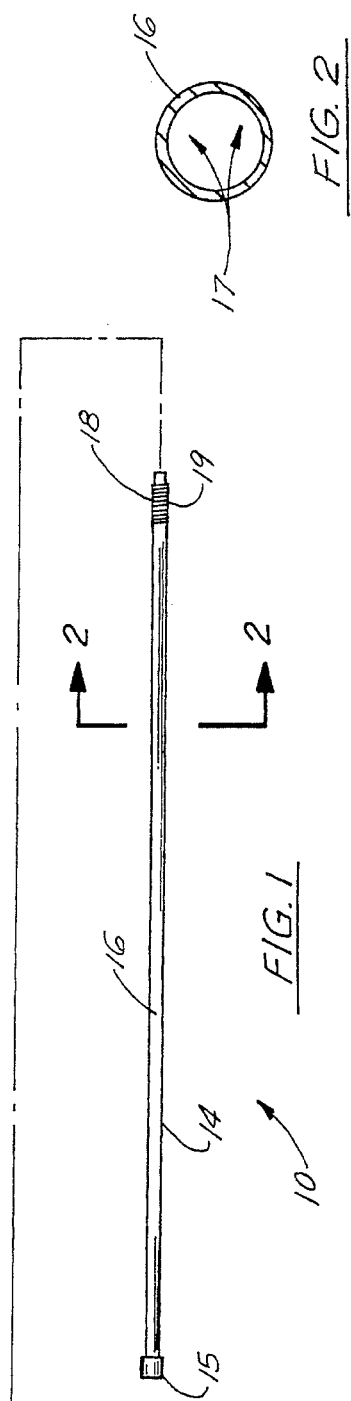
FIG. 2
FIG. 3
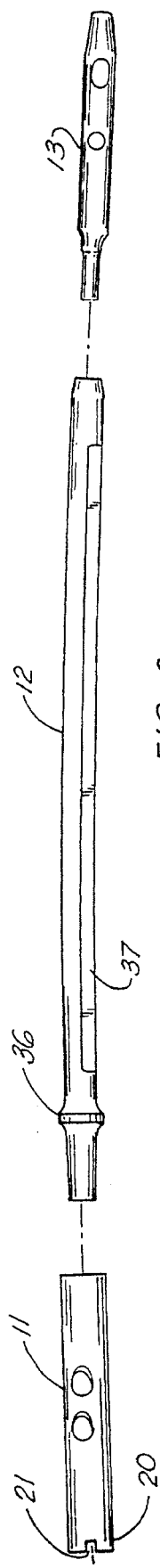
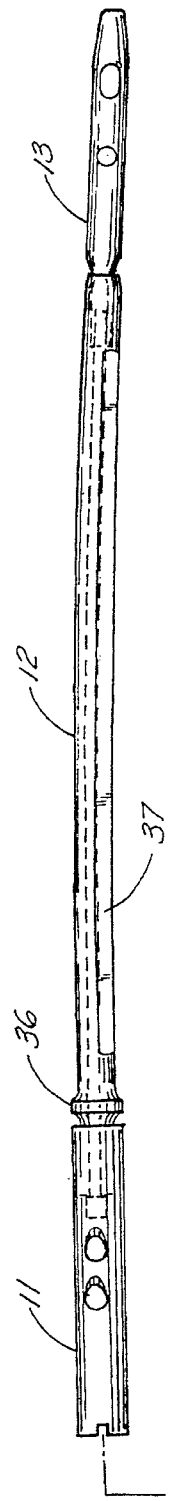
FIG. 1

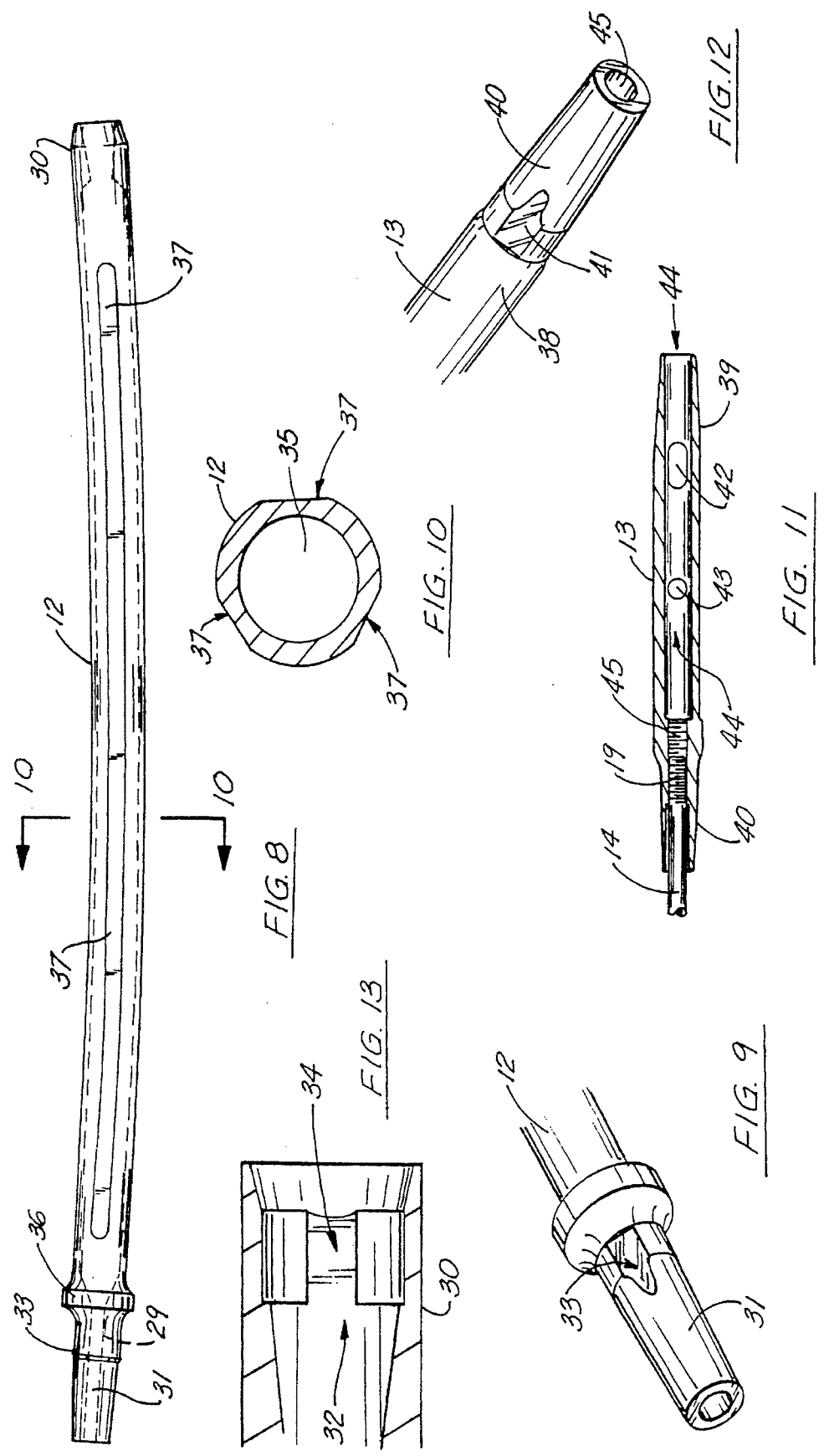

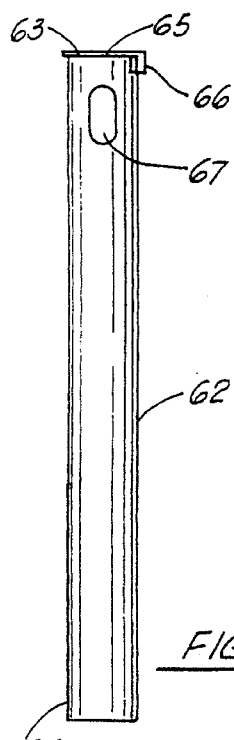
FIG. 18
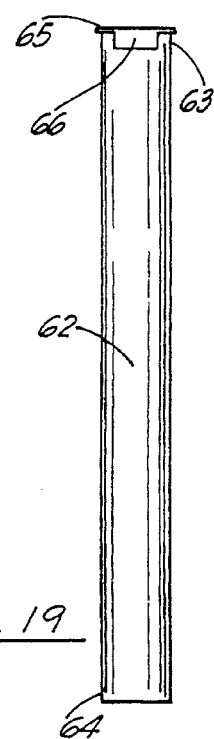
FIG. 19
FIG. 20
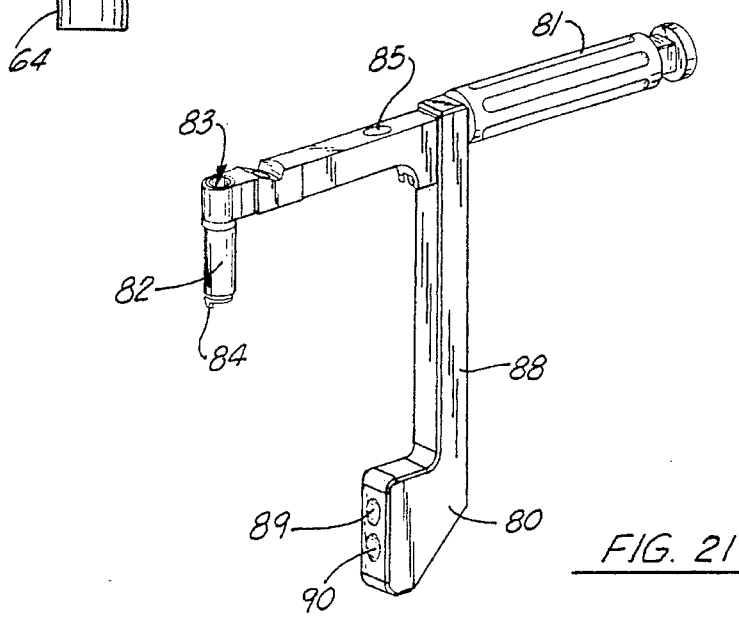
FIG. 21
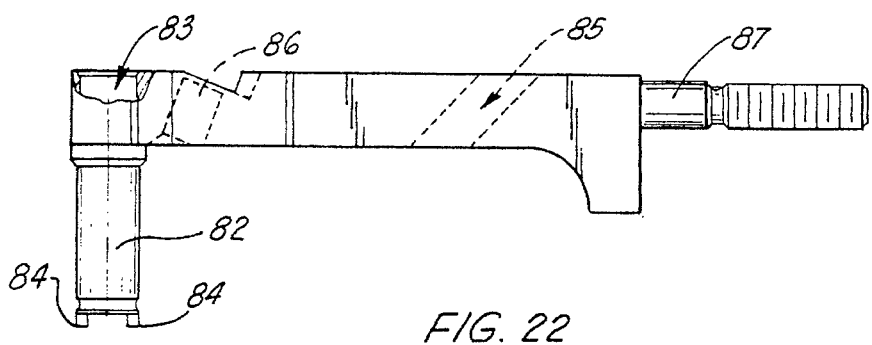
FIG. 22

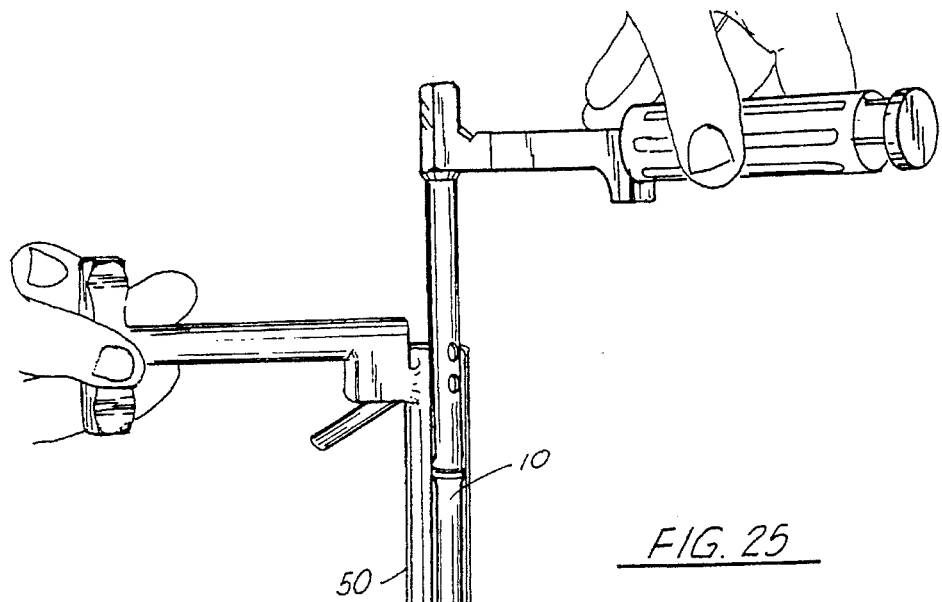
FIG. 25
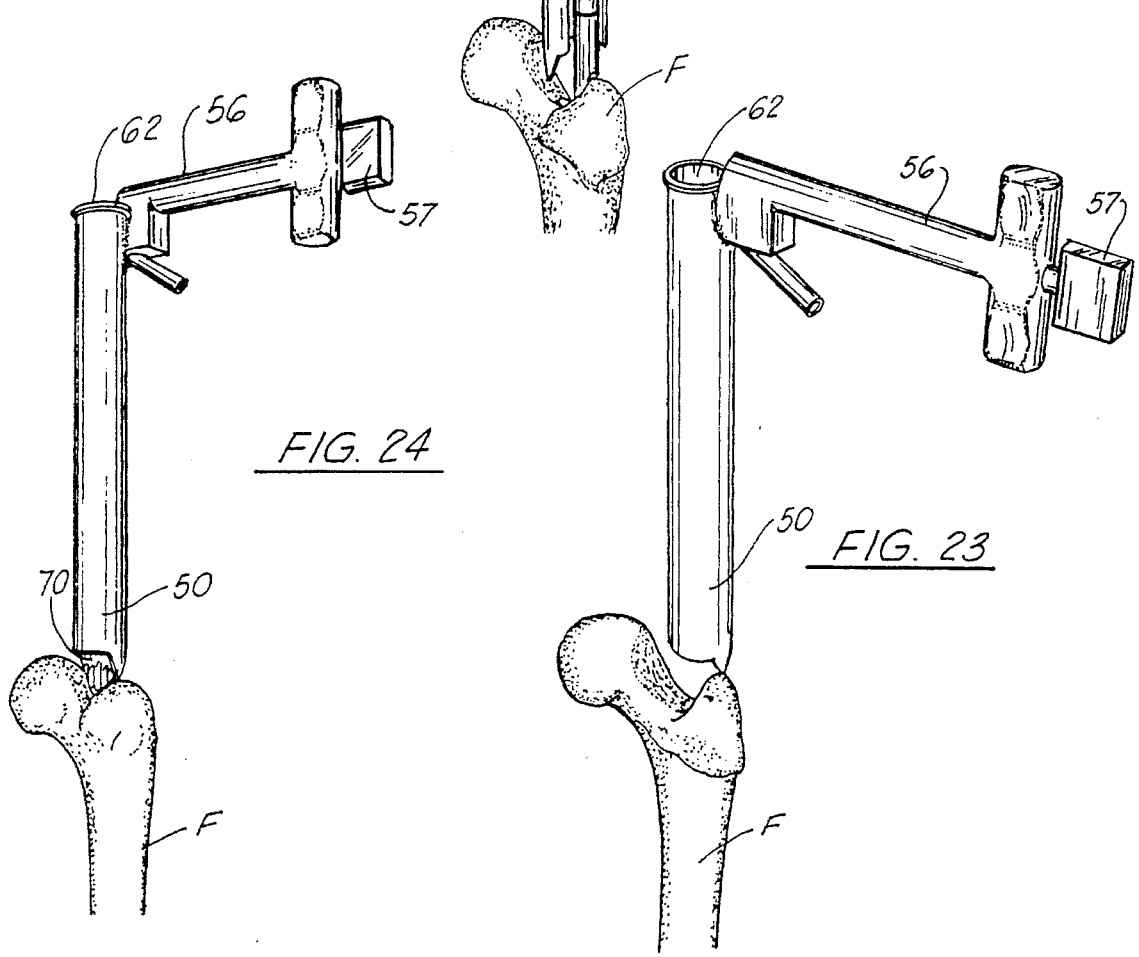
FIG. 24
FIG. 23

CANNULATED MODULAR INTRAMEDULLARY NAIL

SPECIFICATION

1. Field of the Invention

The present invention relates to an intramedullary nail system for the repair of long bone fractures, which has a modular design for enabling a surgeon to assemble a nail or related implant during surgery which most closely fits the patient's needs.

2. Background of the Invention

Intramedullary nails have become the preferred implant treatment in many long bone fracture cases. As the use of intramedullary nails has become more popular, the design of the implants has advanced so that there are particular designs for different types of fractures. Nails having a particular configuration are desirable for certain indications. Because of wide variation of the long bones in patients, the particular style of nail is preferably available in a range of lengths, diameters, and shapes. As a result, the surgeon must have at hand a large inventory of styles and sizes to accommodate the variety of indications. Examples of such styles include, but are not limited to femoral reconstruction, intramedullary hip screw, and femur components of total femoral hips.

One solution to this variation problem is to provide a modular nail system where a surgeon can select various component parts and assemble them to fit a particular patient's needs. Such a system is taught in U.S. Pat. No. 4,805,607 to Engelhardt et al. where a modular intramedullary nail system has elongated base nails and extension members of different lengths and diameters. The base nail is the primary structural component of the system and the extension member is designed to fit on the proximal end of a base nail. By selecting various combinations of base nails and extension members, nails of a desired length and diameter can be constructed. The component parts are locked together by a pair of snap lock springs formed on the proximal end of the base nail, which include engagement tongs with locking barbs at the trailing end which are radially depressed in order to engage a counterbore on the extension member. A screw is inserted through a hole in the modular components after the rod has been implanted for preventing the tongs from disengaging.

Another intramedullary nail is disclosed in the Simpson et al. U.S. Pat. No. 5,122,141, entitled "Modular Intramedullary Nail". In the Simpson patent, an intramedullary nail system and method for providing a capability of creating intramedullary nails of any desired length includes a combination of a small number of base nail members adapted to be joined to any one of a variety of hollow extension nail members. Any selected extension nail member may be axially connected to any selected base nail member in order to prevent axially separation of the members. Additionally, each extension nail members provided with transverse openings adapted to receive a bone screw to secure the intramedullary nail within the bone to be repaired. The extension nail member is infinitely rotationally adjustable about the axis of the base nail member in order to enable the fixation of the extension member with any desired degree of anteversion prior to final assembly of the base nail member with the extension nail member.

The Comte et al. U.S. Pat. No. 4,875,475 shows a device for treating a bone that includes an intramedullary nail adapted to be driven into a hollow bone. The proximal terminal nail segment includes an internal thread and a transversely penetrating longitudinal slot adapted to receive a screw to penetrate through the nail, and to be screw connected to the bone. A distal terminal nail section comprises two transversely throughgoing bores, each adapted to receive a screw to be screw connected with the bone.

The Chapman et al. U.S. Pat. No. 4,776,330 discloses a modular femoral implant system for use in the treatment of femoral disorders resulting from injury, disease, or congenital defects. The modular system includes at least three interconnected components, including an elongated epiphyseal-metaphyseal implant, an intramedullary rod, and an angled side plate having an elongated plate portion adapted to be secured to the outer cortical wall, and a hollow sleeve adapted to extend into the femur.

A French Patent No. 1,031,128 relates to a femoral nail of multiple sections.

The Fischer U.S. Pat. No. 3,846,846 discloses a ball-shaped portion to form part of the hip joint and a second portion that extends from the ball-shaped portion into the femur. The second portion is provided with a passage through which an elongated expander rod is extended which is also to be inserted into an opening in the femur and on the expanded rod is arranged a series of expansion elements in the form of a row which as the expander rod is moved longitudinally of the row are all expanded to anchor the prosthesis to the femur.

An adjustable compression bone screw is disclosed in the Glisson U.S. Pat. No. 4,858,601 that includes a shaft having first and second sections each with an external thread that may be rotated as a unit or independently. The screw includes means adapted to receive a first driving tool for driving the shaft as unit, and further adapted to receive a second driving tool for rotating the second section independently of the first section.

The Tronzo U.S. Pat. No. 4,940,467 discloses a variable length fixation device for insertion into a hole formed in two or more bone fragments and includes a barrel portion and a fastener element. The device is used for repair of the proximal portion of a patient's femur.

The Marcus U.S. Pat. No. 4,622,959, entitled "Multi Use Femoral Intramedullary Nail", discloses an intramedullary nail for use in fractures for the left or right femur and includes a body having a head, an intermediate portion, and a distal tip. Transverse openings are provided in the body near the distal tip and in the head for receiving locking screws. One opening in the head has its axis within the femoral neck and another opening has its axis generally transverse thereto. The nail head has a seat with a transverse locating slot for securing a screw insertion tool in a fixed angular position in which the screw guide on the tool is aligned with one of the screw receiving openings.

The Brumfield U.S. Pat. No. 4,827,917 (incorporated herein by reference), entitled "Femoral Fracture Device," provides an apparatus for treating fractures of the femur that includes a screw and an intramedullary rod. The screw has a threaded portion and a smooth portion. The rod has a head, stem, and longitudinal bore. There is at least one pair of coaxial holes through the stem, transverse to the longitudinal axis of the rod, for receiving first anchoring means such as a nail, screw, or bolt, to secure the rod within the marrow canal of the femur. There are at least a proximal pair of coaxial holes and a distal pair of coaxial holes in the head of the rod in an angled direction toward the femoral head relative to the longitudinal axis of the rod. The distal pair of head holes are adapted to slidingly receive the screw to permit the threaded portion of the screw, in use, to engage the femoral head and to allow sliding compression of a femoral neck or intertrochanteric fracture. An optional second anchoring means which will also allow sliding and compression and an optional set screw are also provided to adapt the fracture device to a variety of applications.

U.S. Pat. No. 4,995,883, issued to DeMane et al. and U.S. Pat. No. 5,108,452, issued to Thomas W. Fallin, both entitled "Modular Hip Prosthesis," disclose a modular hip prosthesis that can be custom fitted to a particular patient by a surgeon prior to surgical insertion. The prosthesis features a body having a neck portion for carrying a rounded head element, a transitional mid-section of the prosthesis body includes generally rectangular and generally rounded cross-sectional areas, and a stem section has a generally rounded cross-sectional area. The stem is tapered to receive a tubular extension sleeve with a hollowed portion corresponding in shape to the stem portion of the prosthesis. The tubular extension sleeve has an open end portion receptive of the lower tapering stem of the prosthesis body. The stem portion including an internal bore, and an attachment in the form of an elongated screw is provided for connection to the stem internal bore for securing the extension sleeve and the prosthesis body together, forming a compressive sealed connection therebetween. Pads can be attached to the transitional midsection of the prosthesis body for increasing the cross-sectional shape of the prosthesis at the transitional midsection. Removable collars can be added to the prosthesis to form a transverse load carrying interface with the upper end of the patient's femur. Frustroconically shaped extension sleeves can be added to the prosthesis neck for extending the neck length.

U.S. Pat. No. 5,047,033, issued to Thomas W. Fallin, entitled "Mill And Guide Apparatus For Preparation Of A Hip Prosthesis," discloses a guide apparatus for preparing the femur of a patient with a rotary mill to receive a femoral hip prosthesis includes a V-shaped guide body having a lower end base portion adapted to extend into the intramedullary canal of the femur and an upper end portion comprised of at least two spaced apart struts so that the overall guide body had a configuration substantially the same as the prosthesis body sought to be implanted in the patient. The lower end of the guide body base provides one or more hemispherical receptacles for holding the hemispherical end portion of a spinning mill bit. A preferably removable transverse guide rail has connection pins at one end portion thereof for forming a connection with the upper end of the guide body at one of the struts, the arm having a curved surface that is adapted to guide the mill bit during preparation of the intramedullary canal of the patient's femur for receiving a hip prosthesis thereafter.

The inventors have determined it is advantageous to have a nail system with greater modularity than in a system such as shown in the Engelhardt patent, and one providing an easier and more secure method of attaching the components, which is assembled without utilizing a screw to hold the components together. And a modular nail that can be driven over a guide rod.

SUMMARY OF THE INVENTION

The present invention is directed to improved intramedullary nails providing a modular intramedullary nail system having three modular components. The components include proximal, central, and distal nail sections. The modular components of the present invention are quickly and easily assembled having joints of high mechanical and torsional integrity.

The modular components of the present invention preferably include a locking mechanism for connecting and locking together adjacent modular components which can quickly provide a positive locking fit that resists relative twisting or rotational movement between the components as well as translation.

Assembly of the modular components of the present invention is achieved by one modular component having a socket with a conical tapered surface adapted to securely engage a cooperating tapered pin or projecting conical surface. The engagement results in a secure taper lock or wedge lock connection which is resistant to translational forces. An example of a modified taper and bore providing such secure connection is a configuration known as a morse taper.

Resistance to rotational movement between adjacent nail section is achieved by providing tooled "flats" adjacent each taper (i.e., a tooled "flat" on the conical socket of one nail section and a corresponding mating tooled "flat" on the engaging conical projection of an adjoining nail section).

In a preferred embodiment, the tooled flats are prepositioned to provide an alignment mechanism to ensure the components are properly assembled in a pre-selected position of anteversion.

A cannulated fastener extends the full length of the assembled nail. The cannulated fastener has a longitudinal bore for tracking a guide wire during installation.

The technique for intramedullary nailing is challenging and is potentially dangerous. The location of the entry portal ultimately determines the location of the locking screws, which is not critical in the femoral mode but is very critical in the recon mode. The surface of the bone is angled and surrounded by muscles. Typical open incision technique has a guide road in the muscles to locate the entry portal, which slips on the angled bone and the muscles make fine adjustment of the thin guide rod difficult and can be very time consuming, adding to the time the patient must be under anesthesia. If the entry portal is off of the optimal placement, the later portion of surgery, placement of the screws in the femoral head, gets very difficult and can be very time consuming and lead to poor outcomes.

The procedure is very bloody, especially the reaming of the canal. It is not uncommon for the floor to have standing pools of blood and have the surgical team splattered heavily. The risk of disease transfer is high and the cleaning costs are high also.

Many patients are obese and when in the position to have a femur nailed have many inches of soft tissue on the lateral aspect of their thigh. The positioning of a conventional recon drill guide is difficult due to this tissue and frequently the skin must be opened for the length of the drill guide, about 8 inches, to allow the drill guide to be advanced to the full depth.

BRIEF DESCRIPTION OF THE DRAWINGS

In order to acquire a better understanding of the invention, reference may be had to a detailed description of exemplary embodiments set forth below, to be considered along with the appended drawings, in which:

FIG. 1 is a side, partially exploded view of the preferred embodiment of the apparatus of the present invention;

FIG. 2 is a sectional view taken along lines 2-2 of cannulated fastener 16 of FIG. 1;

FIG. 3 is an exploded side view of the preferred embodiment of the apparatus of the present invention;

FIG. 8 is a side view of the preferred embodiment of the apparatus of the present invention illustrating the central nail section thereof;

FIG. 9 is a fragmentary perspective view of the central nail section of FIG. 8;

FIG. 10 is a sectional view taken along lines 10 of FIG. 8;

FIG. 11 is a fragmentary sectional side view of the preferred embodiment of the apparatus of the present invention illustrating the distal nail section thereof;

FIG. 12 is a fragmentary perspective view of the distal nail section of FIG. 11;

FIG. 13 is a fragmentary sectional view of the central nail section of FIG. 8.

FIG. 18 is an elevational view of the reaming sheath portion of the instrumentation used to install the preferred embodiment of the apparatus of the present invention;

FIG. 19 is another elevational view of the reaming sheath portion of the instrumentation as used to install the intramedullary nail of the present invention;

FIG. 20 is a top view of the reaming sheath portion of the instrumentation as used to install the intramedullary nail of the present invention;

FIG. 21 is a perspective view of the modular drill guide portion of the instrumentation used to install the modular intramedullary nail of the present invention;

FIG. 22 is a fragmentary view illustrating a portion of the modular drill guide of FIG. 21; and FIGS. 23–25 are perspective views illustrating the surgical method steps of implanting the modular intramedullary nail of the present invention using the instrumentation of FIGS. 14–22.

DESCRIPTION OF THE EXEMPLARY EMBODIMENTS

Figure 4:
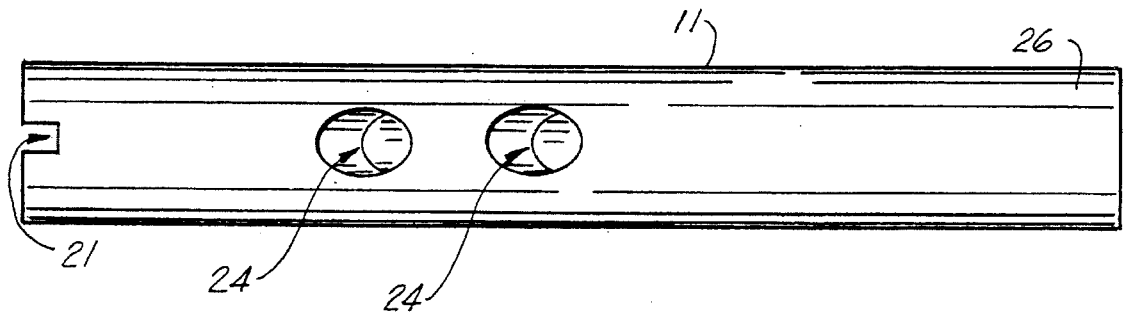
FIG. 4 is a fragmentary side view of the preferred embodiment of the apparatus of the present invention illustrating the proximal nail section thereof.

FIGS. 1–3 illustrate the preferred embodiment of the apparatus of the present invention illustrated generally by the numeral 10. Modular intramedullary 10 includes three sections that are connectable end-to-end. The three sections include proximal nail section 11, central nail section 12, and distal nail section 13. The three sections are secured together using cannulated fastener 14.

In FIG. 1, cannulated fastener 14 includes an enlarged head 15, an elongated cylindrical hollow shaft 16, and a threaded distal end portion 18 having external threads 19 thereon. Fastener 14 has a continuous open ended cylindrically-shaped bore 17 that extends its full length.

Proximal nail section 11 includes a proximal end portion 20 that carries a pair of circumferentially spaced apart slots 21. The slots 21 can receive an insertion tool such as, for example, a drill guide, attached using slots and a bolt (not shown) that communicates with an internally threaded section 23 of open ended longitudinal bore 22.

Figure 5:
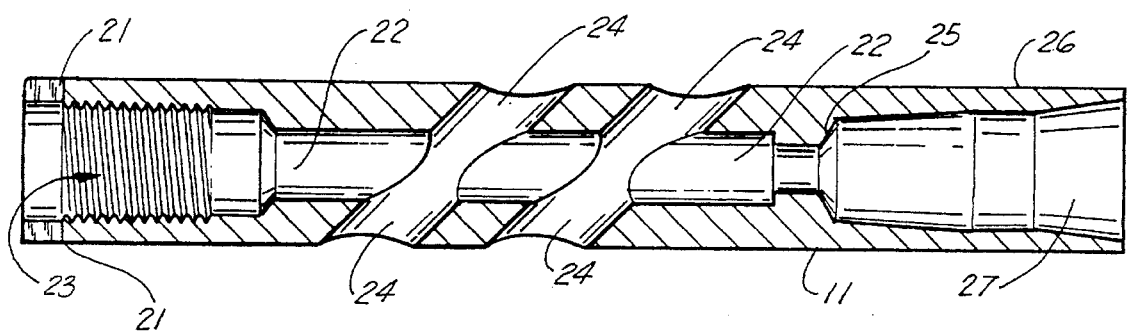
FIG. 5 is a longitudinal sectional view of the preferred embodiment of the apparatus of the present invention illustrating the proximal nail section thereof.
Figure 6:
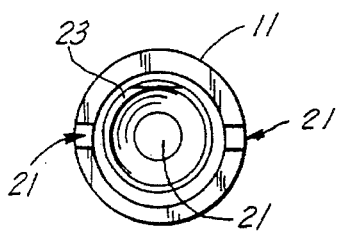
FIG. 6 is an end view of the proximal nail section of FIGS. 4 and 5.
Figure 7:
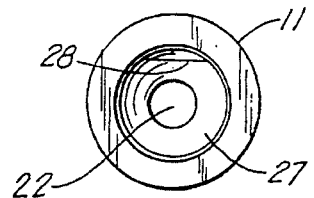
FIG. 7 is another end view of the proximal nail section of FIGS. 4 and 5.

Bore 22 is intersected at an acute angle (approximately forty-five degrees (45°) for example) by a passageway that is defined by aligned pairs of diagonal openings 24 as shown in FIG. 5. Openings 24 can receive bone screws (not shown). Bone screws can be inserted in one direction for using the nail in the femoral mode and by inserting screws in the opposite direction the nail can be used in the reconstructive mode.

Distal end portion 26 of proximal nail section 11 includes a conical section 27 for forming a taper lock connection with central nail section 12. In order to prevent rotation between the sections 11, 12, a tooled flat surface 28 is formed on the distal end 26 of proximal nail section 11 at conical socket 27. A similar tooled flat surface is provided on the proximal end of central section 12. When the proximal 11 and central 12 sections are assembled together, the corresponding tooled flat surfaces 28, 33 abut and align to define a self-orienting, anti-rotation connection between adjoining nail sections 11, 12.

In FIGS. 8–9, central nail section 12 is shown. Central nail section 12 includes proximal end 29, distal end, and can have longitudinal flat external surfaces 37 (see FIGS. 8 and 10). Proximal end 29 includes a conical projection 31 for communicating with the socket 27 of proximal nail section 11. A tooled flat surface 33 on conical projection 31 cooperates with the tooled flat surface 28 of conical socket section 27 upon assembly of proximal 11 and central 12 nail sections.

The corresponding tooled flat surfaces 28, 33 insure that nail sections 11, 12, do not rotate with respect to one another. Further, these tooled flat surfaces 28, 33 align and abut upon assembly so that the degree of anteversion of the nail sections 11, 12 is preset prior to surgical insertion. The tooled flat surfaces 28, 33 define a self-orienting structure when the nail sections 11, 12 are assembled. The conical surfaces 27, 31 define a locking taper connection that locks the two nail sections 11, 12 together upon assembly. Proximal end 29 can have an annular collar 36 that provides a gripping surface during disassembly.

The distal end 30 of central nail section 12 provides a conical socket 32 for receiving distal end section 13. Conical socket 32 includes a tooled flat surface 34 that cooperates with a similar and corresponding tooled flat surface on proximal end 38 of distal nail section 13. Central nail section 12 includes a longitudinal open ended bore 35 that extends the full length of the nail section 12.

The central section 12 of the nail 10 preferably has a wall thickness equal to nails that are clinically effective. Wall thickness is related to nail stiffness which affects the healing rate of the fractured bone. Manufacture of the taper requires a small inside diameter section of the nail to be present prior to machining the taper. Therefore the nail section 12 is made with a larger outside diameter than will be required, allowing a large inside diameter with corresponding correct wall thickness. The end 30 of the nail section 12 that is to form the taper is swaged so the inside and outside diameter of the nail is reduced. The taper 32 is machined out of the swaged material. The nail section 12 then has a taper 31, 32 on each end and a larger diameter in between. The central nail component has a wall thickness of between about 1.0 and 2.0 mm. The central nail section preferably provides a pair of smaller diameter bore sections at its opposing end portions. The nail components also have a shaped projection 28 on the male connector section and a shaped socket on the female connector section. The central nail component is about twice as long as, preferably at least twice as long as the proximal nail component. The central nail component is about twice as long as the distal nail component. In the preferred embodiment, the central component is between 125 and 300 mm in length. The three assembled nail components provide an overall length of between 200 and 500 mm in the preferred embodiment.

In FIG. 11, distal nail section 13 is shown. Distal nail section 13 includes a proximal end 38 and a distal end 39. The proximal end portion 38 has a conical projection 40 with a tooled flat surface 41 thereon that corresponds to and registers against tooled flat surface 34 of socket 32 upon assembly of central nail section and distal nail section 13. Lateral openings 42 extend transversely through distal nail section 13. Similarly, lateral openings 43 extend transversely through distal nail section 13 at a position longitudinally spaced away from the openings 42. Each of the openings 42, 43 communicates with longitudinal bore 44 that extends the full length of nail section 13. At the proximal end 38 of distal nail section 13, internally threaded section 45 communicates with bore 44. Internally threaded section 45 has internal threads that corresponds to the external threads 19 of cannulated fastener 14. Upon assembly, the threads 19 engage the threads 45.

The enlarged head 15 of cannulated fastener 14 registers against annular shoulder 25 that defines an intersection between bore 22 and internal threads 23 of proximal section 11, as shown in FIG. 5. Thus, upon assembly, the cannulated fastener 14 secures the three nail sections 11–13 together, forming a taper lock or wedge lock connection between the sections. Cannulated fastener 14 provides an internal bore 17 so that a guide wire can be used to correctly channel placement of the nail sections 11–13 in a fractured bone. The cannulated fastener 14 holds the nail sections together when the nail sections are removed.

Figure 14:
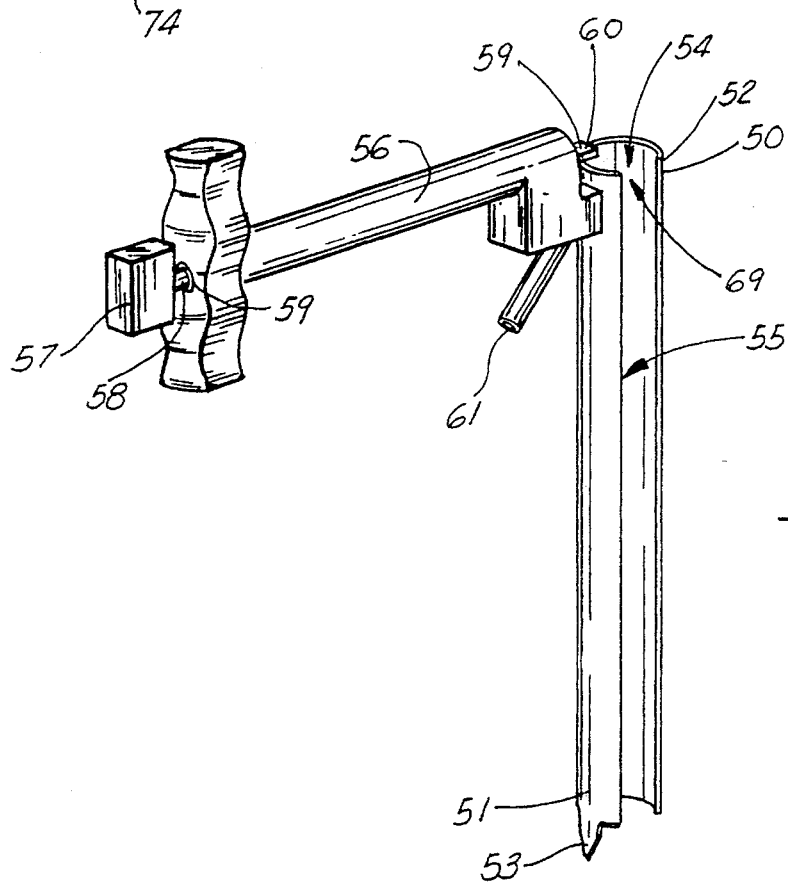
FIG. 14 is a perspective fragmentary view of the instrumentation portion of the apparatus of the present invention showing the entry portal tool portion thereof.

In FIGS. 14–22, instrumentation is shown that is used to install the modular intramedullary nail 10 of the present invention that is disclosed in FIGS. 1–13. In FIG. 14, entry portal tool 50 is shown having a distal end 51 and a proximal end 52. The distal end 52 includes a bone engaging spike 53 that is placed upon the proximal end of the patient's femur to begin surgical installation of the modular intramedullary nail 10. The proximal end has a handle 56.

Entry portal tool 50 has an elongated longitudinal bore 54 and a longitudinal slot 55 formed in the portal tool 50 as shown in FIG. 14. Handle 56 can be used by the surgeon to manipulate the entry portal tool 50. The handle includes an elongated open ended bore 59 that holds elongated shaft 58 with wing nut 57 secured to one end thereof. Shaft 58 slides in bore 59 and has an end 60 that extends to proximal end 52 of entry portal tool 50. The shaft end 60 defines a stop for holding cannulated obturator 70 and reaming sheath 62 in position after they have been assembled to entry portal tool 50. Suction port 61 is a flow channel that extends to bore 54. The port 61 can be attached to a flexible hose or tubing and a suction machine for continuously moving blood that is generated during the operative procedure and received within the bore 68 of reaming sheath 62.

Reaming sheath 62 is an elongated cylindrically-shaped hollow sheath having a proximal end 63 and a distal end 64. The proximal end 63 has an annular collar 65 and includes a thickened flange 66 portion that registers with the slot 55 of entry portal tool 50 thus preventing any rotation of sheath 62 when placed in bore 54 as occurs during use. The flange 66 registers with slot 55 at proximal end 52, the location of flange 66 upon assembly being designed by the numeral 69 as the position for the flange. This positioning of flange 66 in slot 55 at 69 aligns suction port 67 with suction port 61.

Figure 15:
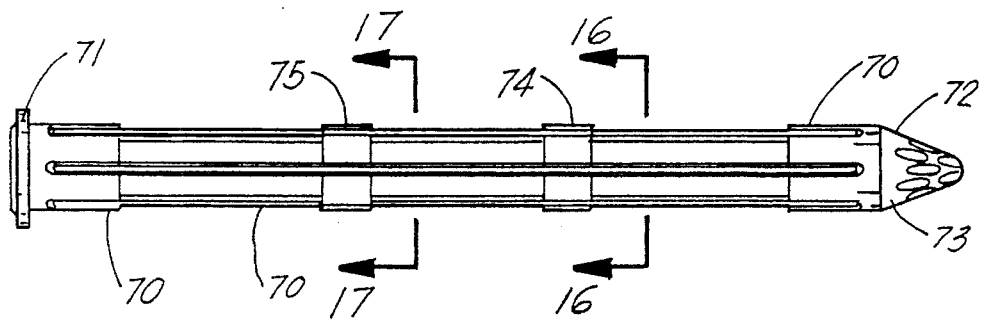
FIG. 15 is a side fragmentary view of the instrumentation portion of the apparatus of the present invention illustrating the cannulated obturator.
Figure 16:
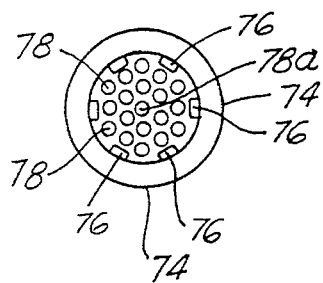
FIG. 16 is a sectional view taken along lines 16—16 of FIG. 15.
Figure 17:
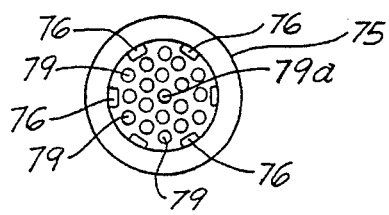
FIG. 17 is a sectional view taken along lines 17—17 of FIG. 15.

In FIGS. 15–17, cannulated obturator 70 is shown, having a proximal end portion 71 and a distal end portion 72. Proximal end 71 is in the form of a cylindrical hub with openings therein like hubs 74, 75 of FIGS. 16–17. Distal end 72 includes a conical tip 73. A pair of cylindrical perforated hubs 74, 75 are placed longitudinally between the proximal 71 and distal 72 ends of cannulated obturator 70.

Each of the hubs 74, 75 and the conical tip 73 include correspondingly placed radially and circumferentially placed openings. The openings 77, 78, 79 align along parallel lines that are parallel with the central longitudinal axis of cannulated obturator 70. This provides a matrix of aligned guide openings that can be selected by the surgeon for placement of a guide wire therethrough.

During use, the surgeon places the reaming sheath 62 in entry portal tool 50 bore 54. The surgeon then places the cannulated obturator 70 within the bore 68 of reaming sheath 62. The surgeon places the conical tip 73 and bone spike 53 on the proximal femur and aligns the central longitudinal axis of reaming sheath 62 and cannulated obturator 70 with the central longitudinal axis of the patient's intramedullary canal (See FIGS. 23–24). The surgeon can then place a guide wire (commercially available) through a selected set of aligned openings in the hubs 74, 75 and conical tip 73. An aligned opening is also provided in proximal end 71 of obturator 70.

It should be understood that when the surgeon places the guide wire through a selected set of the openings, the guide wire is maintained in parallel relationship with the central longitudinal axis of the obturator 70. Thus, a single guide wire extends through four aligned openings and along a path parallel with the central longitudinal axis of obturator 70. The four openings are respectively in proximal end portion 71, hubs 74, 75 and conical tip 73. The surgeon can then thrust the guide wire up to a few inches into the femur and examine position of the wire fluoroscopically. If the guide wire position is unacceptable, the surgeon then moves the guide wire radially and/or circumferentially a few millimeters to select a different set of aligned openings. Each time the surgeon does select a different set of aligned openings, the guide wire is still maintained in parallel relationship with the tool body because of the corresponding axial alignment of corresponding holes in the conical tip 73, hubs 74, 75, and proximal end 71 of the obturator 70. This allows the surgeon to move the guide wire circumferentially and radially to a desired position until the surgeon has chosen a suitable location for the guide wire. The guide wire defines the position of cut for a cannulated drill reamer (commercially available) that tracks the guide wire once the obturator 70 is removed.

After the surgeon has selected a desirable location for the guide wire, the surgeon then removes obturator 70, leaving portal tool 50 and reaming sleeve 62. The surgeon then places a standard commercially available cannulated reamer over the guide wire and drills an opening through the femur that will accommodate modular intramedullary nail 10.

A plurality of longitudinal struts 76 connect conical end 73, hubs 74, 75, and proximal end 71 of obturator 70. Longitudinal struts 76 are positioned at the peripheral portion of obturator 70 so as not to interfere with the surgeon's selection of aligned openings for placement of the guide wire during use.

In FIGS. 15–17, the plurality of radially and circumferentially spaced openings in conical tip 73 are designated by the numeral 77. The openings in hub 74 (FIG. 16) are designated by the numeral 78. The openings in hub 75 (FIG. 17) are designated by the numerals 79.

In FIGS. 16 and 17, it can be seen that the openings 78 and 79 are correspondingly placed with reference to the central longitudinal axis of obturator 70 which represents the center openings 78a, 79a respectively of FIGS. 16 and 17. Each of the openings 77, 78, 79 are in the same radial and circumferential position. The pattern of openings 77 in conical tip 73 is the same as the patterns of openings 78, 79 in FIGS. 16–17, and the same pattern of openings is provided in proximal end 71. This insures that a guide wire inserted through any selected set of aligned openings in the cannulated obturator will always be parallel to the central longitudinal axis of the obturator 70.

FIGS. 21–22 show modular drill guide 80. Modular drill guide 80 includes a handle 81, recon drop 88, stem 87, hollow barrel 82, and a bore 83. Bore 83 is open ended for receiving an assembly bolt that will secure modular intramedullary nail 10 to barrel 82 at projections 84. The projections 84 are preferably spaced circumferentially about 180° apart and correspond to the slots 21 on the proximal end 20 of modular intramedullary nail 10 upon assembly. Using the bolt to engage threads 23 of proximal nail component 11, and using slots 21 and projections 84 for radial alignment, the central longitudinal axis of bore 83 aligns with the central longitudinal axis of nail 10 proximal section 11.

Once nail 10 is secured to barrel 82, the surgeon can then place the assembled nail 10 and its attached modular drill guide 80 through entry portal tool 50 (see FIG. 25). Before placement of the nail 10, obturator 70 and reaming sleeve 62 are removed from bore 54 of entry portal tool 50. Slot 55 defines an opening that can be occupied by modular drill guide 80 as shown in FIG. 24. Diagonal opening 85 in drill guide 80 can receive a drill for forming a diagonal opening in the patient's bone tissue. The opening 85 and the projections 84 are positioned so that a drill tracking opening 85 will intersect one of the diagonal openings in the proximal end of modular nail 10 for using the nail in the femoral mode.

The entry portal tool 50 allows precise placement of the guide rod with little interference from the muscles and is less sensitive to glancing off the angled surface of the bone. The aligned holes of the obturator 70 allow exact placement of the pin in the position required for proper recon nail placement. Use of the entry portal tool 50 can reduce initial time to find the entry portal and secondary time later in surgery that would be required for screw placement.

Use of the entry portal tool 50 reduces the blood exposure to the surgical team, reducing disease risk, and the blood may be collected neatly and perhaps reinfused.

The following table lists the parts numbers and parts descriptions as used herein and in the drawings attached hereto.

PARTS LIST

| Part Number | Description |
| --- | --- |
| 10 | modular intramedullary nail |
| 11 | proximal section |
| 12 | central section |
| 13 | distal section |
| 14 | cannulated fastener |
| 15 | head |
| 16 | cylindrical hollow shaft |
| 17 | continuous open-ended bore |
| 18 | threaded distal end |
| 19 | external threads |
| 20 | proximal end |
| 21 | slot |
| 22 | open-ended longitudinal bore |
| 23 | internally threaded section |
| 24 | diagonal openings |
| 25 | annular shoulder |
| 26 | distal end |
| 27 | conical socket section |
| 28 | tooled flat surface |
| 29 | proximal end |
| 30 | distal end |
| 31 | conical projection |
| 32 | conical socket |
| 33 | tooled flat surface |
| 34 | tooled flat surface |
| 35 | bore |
| 36 | annular collar |
| 37 | longitudinal flat surface |
| 38 | proximal end |
| 39 | distal end |
| 40 | conical projection |
| 41 | tooled flat surface |
| 42 | lateral opening |
| 43 | lateral opening |
| 44 | longitudinal bore |
| 45 | internal threads |
| 50 | entry portal tool |
| 51 | distal end |
| 52 | proximal end |
| 53 | bone engaging spike |
| 54 | longitudinal bore |
| 55 | longitudinal slot |
| 56 | handle |
| 57 | wing nut |
| 58 | shaft |
| 59 | bore |
| 60 | shaft end |
| 62 | reaming sheath |
| 63 | proximal end |
| 64 | distal end |
| 65 | annular collar |
| 66 | flange |
| 67 | suction port |
| 68 | longitudinal bore |
| 69 | flange location |
| 70 | cannulated obturator |
| 71 | proximal end |
| 72 | distal end |
| 73 | conical tip |
| 74 | cylindrical perforated hub |
| 75 | cylindrical perforated hub |
| 76 | longitudinal strut |
| 77 | tip openings |
| 78 | hub openings |
| 78a | center opening |
| 79 | hub openings |
| 79a | center opening |
| 80 | modular drill guide |
| 81 | handle |
| 82 | barrel |
| 83 | bore |
| 84 | projections |
| 85 | diagonal opening |
| 86 | opening |

| Part Number | Description |
|---|---|
| 87 | stem |
| 88 | recon drop |
| 89 | opening |
| 90 | opening |
| F | femur |

The foregoing description should be considered exemplary of the invention and not restrictive. It should also be understood that improvements and modifications can be made to the invention without departing from the spirit and scope of the invention as defined in the appended claims.

We claim:

1. A modular intramedullary nail, comprising:
   a) a proximal nail component having an open ended longitudinal bore;
   b) a distal nail component having an open ended longitudinal bore;
   c) a central nail component having an open ended longitudinal bore and having proximal and distal end portions that are respectively connected during use to the proximal and distal nail components, said central nail section bore being of a generally uniform diameter along a majority of its length;
   d) connecting means for securing the proximal and distal nail components to the proximal and distal end portions of the central nail component, the connection means including corresponding conical socket and conical projecting end portions of adjoining nail components that can be fitted together and secured with force; and
   e) the connecting means including self orienting means on the proximal add distal nail components adjacent the respective conical socket and conical projecting end portions for resisting relative rotational movement between the components;
   f) a cannulated fastener extending through a portion of the bore of the proximal and distal nail components, and through the entire length of the bore of the central nail component, the fastener having a proximal end portion with means thereon for gripping the proximal nail component, a distal end portion with external threads thereon, and an open ended longitudinal bore; and
   g) the proximal end of the bore of the distal nail component having an internally threaded bore section that can threadably engage the external threads of the cannulated fastener.

2. The modular nail of claim 1, wherein the central nail component has a wall thickness of between about 1.0 and 2.0 millimeters along a majority of its length.

3. The modular nail of claim 1, wherein the self-orienting means includes corresponding tooled flat surfaces on adjacent and connecting conical socket and conical projecting portions.

4. The modular nail of claim 1, wherein the proximal nail component has a partially internally threaded bore section.

5. The modular nail of claim 1, wherein the conical socket and conical projecting end portions are generally frustro-conical in shape.

6. The modular nail of claim 1, wherein said central nail component has an annular external collar at one end portion thereof.

7. The modular nail of claim 1, wherein the self-orienting means includes at least one set of cooperating shaped flat surfaces.

8. The modular nail of claim 7, wherein said at least one set of shaped flat surfaces is formed on each conical projecting portion.

9. The modular nail of claim 1, wherein the proximal nail component has at least one transverse opening therethrough.

10. The modular nail of claim 1, wherein the distal nail component has at least one transverse opening therethrough.

11. The modular nail of claim 1, wherein the self orienting means includes a shaped at one end portion projection on the male connector section and shaped socket on the female connector section, the projection and socket being shaped to prevent relative rotational movement.

12. The modular nail of claim 1, wherein the distal nail component has a first and second end portion, the first end portion having a conical projecting end portion, and the second end portion is frustroconically shaped.

13. The modular nail of claim 1, wherein the central nail component is curved longitudinally.

14. The modular nail of claim 1, wherein the central nail component is about twice as long as the proximal nail component.

15. The modular nail of claim 1, wherein the central nail component is at least twice as long as the proximal nail component.

16. The modular nail of claim 1, wherein the central nail component is about twice as long as the distal nail component.

17. The modular nail of claim 1, wherein the central nail component is at least twice as long as the distal nail component.

18. The modular nail of claim 1, wherein the central nail component is between 125 and 300 mm in length.

19. The modular nail of claim 1, wherein the assembled nail components have an overall length of between 200 and 500 mm.

* * * * *

UNITED STATES PATENT AND TRADEMARK OFFICE
CERTIFICATE OF CORRECTION

PATENT NO. : 5,489,284
DATED : Feb. 6, 1996
INVENTOR(S) : Anthony James, Harry Lee, John R. Pepper, Thomas A. Russell It is certified that error appears in the above-identified patent and that said Letters Patent is hereby corrected as shown below:

Claim 1, step c), line 6, after "length" insert --, and of a smaller diameter at each end portion thereof--.

Claim 1, step d), line 6, after "with force;" delete "and".

Claim 1, step e), line 2, change "add" to --and--.

Claim 1, step g), line 3, delete "threadably".

Signed and Sealed this

Twenty-fourth Day of February, 1998

Attest:

BRUCE LEHMAN

*Attesting Officer*  *Commissioner of Patents and Trademarks*